(12) United States Patent
Blomqivst et al.

(10) Patent No.: US 8,535,215 B2
(45) Date of Patent: Sep. 17, 2013

(54) IMPLANTABLE HEART MONITORING DEVICE AND METHOD

(75) Inventors: Andreas Blomqivst, Spånga (SE); Michael Broomé, Ekerö (SE)

(73) Assignee: St. Jude Medical AB, Jarfalla (SE)

( * ) Notice: Subject to any disclaimer, the term of this patent is extended or adjusted under 35 U.S.C. 154(b) by 204 days.

(21) Appl. No.: 13/060,649

(22) PCT Filed: Aug. 29, 2008

(86) PCT No.: PCT/SE2008/000490
§ 371 (c)(1),
(2), (4) Date: Feb. 24, 2011

(87) PCT Pub. No.: WO2010/024739
PCT Pub. Date: Mar. 4, 2010

(65) Prior Publication Data
US 2011/0160605 A1 Jun. 30, 2011

(51) Int. Cl.
*A61N 1/00* (2006.01)
(52) U.S. Cl.
USPC .............................................. 600/24
(58) Field of Classification Search
USPC .............................................. 607/24
See application file for complete search history.

(56) References Cited

U.S. PATENT DOCUMENTS

| | | | |
|---|---|---|---|
| 4,535,774 A * | 8/1985 | Olson | 607/24 |
| 4,867,162 A * | 9/1989 | Schaldach | 607/17 |
| 5,025,795 A * | 6/1991 | Kunig | 600/526 |
| 6,292,693 B1 | 9/2001 | Darvish et al. | |
| 6,314,323 B1 | 11/2001 | Ekwall | |
| 6,714,811 B1 | 3/2004 | Padmanabhan et al. | |
| 6,904,313 B1 | 6/2005 | Snell | |
| 2001/0012953 A1 | 8/2001 | Molin et al. | |
| 2001/0021864 A1 | 9/2001 | Molin | |
| 2003/0220582 A1 | 11/2003 | Zhu et al. | |
| 2007/0021678 A1 | 1/2007 | Beck et al. | |
| 2007/0049835 A1 | 3/2007 | Goode, Jr. | |
| 2007/0055170 A1 | 3/2007 | Lippert et al. | |
| 2007/0100249 A1 | 5/2007 | Torpo et al. | |

OTHER PUBLICATIONS

"Hemodynamic Effects of Tachycardia in Patients with Relaxation Abnormality: Abnormal Stroke Volume Response as an Overlooked Mechanism of Dyspnea Associated with Tachycardia in Diastolic Heart Failure," Sohn et al., Journal of the American Society of Echocardiography (2007) pp. 171-176.
"Effects of Heart Rate on Ventricular Size, Stroke Volume, and Output in the Normal Human Fetus: A Prospective Doppler Echocardiographic Study," Kenny et al., Circulation, vol. 1 (1987) pp. 52-58.

* cited by examiner

*Primary Examiner* — Christopher D Koharski
*Assistant Examiner* — Philip Edwards

(57) ABSTRACT

In an implantable heart monitoring device and method, particularly for monitoring diastolic dysfunction, a control circuit (a) detects the heart rate, (b) derives information correlated to the stroke volume of the heart at the detected heart rate, and (c) stores the detected heart rate and the derived information correlated to the stroke volume in a memory. The control circuit automatically implements (a), (b) and (c) at a number of different occasions for a number of different, naturally varying heart rates, so that the memory contains information indicating the stroke volume as a function of the heart rate.

11 Claims, 3 Drawing Sheets

IMPLANTABLE HEART MONITORING DEVICE AND METHOD

BACKGROUND OF THE INVENTION

1. Field of the Invention

The present invention relates to an implantable heart monitoring device, with which it is possible to monitor the heart condition. The invention also concerns a corresponding method.

2. Description of the Prior Art

Several different devices for monitoring the performance of a heart are known. Often these devices are also able to deliver stimulation pulses to the heart. The devices are often able to sense the electrical activity in the heart. It is also known to determine an impedance value measured between different electrodes positioned in or at the heart. It is also known to sense other physiological parameters, such as pressure, oxygen level etc.

US 2001/0012953 A1 describes bi-ventricular pacing. An impedance may be measured between electrodes on the right and the left sides of the heart. The variation of the impedance with time is detected. The detected impedance variation may be used in order to synchronise the contraction of the ventricles.

US 2001/0021864 A1 describes different manners of using the proximal and distal electrodes of different leads in order to inject a current and to measure an impedance. The measured impedance value may be used in order to maximise the cardiac flow.

US 2007/0049835 A1 relates to an implantable cardioverter-defibrillator or pacemaker whose standard circuitry is used to trend a physiological cardiac parameter using intracardiac impedance measurements.

US 2007/0100249 A1 describes an implantable medical apparatus for detecting diastolic heart failure, DHF. The apparatus includes circuitry for determining, as the DHF parameter, the time duration of a predetermined phase of diastole.

US 2007/0055170 A1 describes a device for detecting the state of a heart on the basis of intracardial impedance measurement. The device has an impedance measuring unit as well as an analysis unit, which is connected to the impedance measuring unit and is implemented to derive a cardiac function parameter from a time curve of the impedance ascertained using the impedance measuring unit. The analysis unit derives a cardiac function parameter characterizing the behaviour of a heart during the diastole.

U.S. Pat. No. 6,314,323 describes a heart stimulator in which the cardiac output is determined by measuring the systolic pressure.

The article "Hemodynamic Effects of Tachycardia in Patients with Relaxation Abnormality: Abnormal Stroke Volume Response as Overlooked Mechanism of Dyspnea Associated with Tachycardia in Diastolic Heart Failure" by Dae-Won Sohn et al., Journal of the American Society of Echocardiography, February 2007, pp. 171-176, describes a comparative study of two groups of individuals: healthy individuals and individuals with stable relaxation abnormality. The article describes how left ventricular pressure and stroke volume varies for the two groups when the heart is paced with 80 beats per minute and 120 beats per minute.

SUMMARY OF THE INVENTION

An object of the present invention is to provide an implantable heart monitoring device with which it is possible to detect or monitor the status of the heart of a patient who suffers from a heart failure, in particular a diastolic dysfunction. A further object is to provide such a device, which with quite simple means makes it possible to detect or monitor the status of the heart condition of a patient who suffers from such heart deficiency.

The above objects are achieved by an implantable heart monitoring device having at least one memory and a control circuit configured to communicate with a number of implanted electrode and/or sensor members adapted to be positioned in a heart or in relation to a heart of a living being such that the control circuit, by means of these members, is able to detect the heart rate of the living being and to derive information correlated to the stroke volume of said heart, wherein the control circuit is configured to carry out the following steps:

a) detect the heart rate, b) derive said information correlated to the stroke volume at said detected heart rate, and c) store the detected heart rate and the derived information correlated to the stroke volume in said memory, wherein the control circuit is configured to automatically carry out steps a) to c) at a number of different occasions at different, naturally varying, heart rates, such that the memory contains information that indicates the stroke volume as a function of the heart rate.

The information concerning the stroke volume as a function of the heart rate constitutes important information about the status of the heart. In particular, when a patient suffers from a diastolic dysfunction, the stoke volume tends to decrease more with increasing heart rate than for a patent without such dysfunction. The more the stroke volume decreases with increasing heart rate, the worse is the dysfunction in question. Since according to the present invention, information concerning the stroke volume as a function of the heart rate is obtained, the device according to the invention provides important information concerning the status of the heart. Furthermore, the device carries out the mentioned steps automatically, which means that for example no physician needs to be present for carrying out the steps. The device does not have to have a complicated construction in order to provide the information. For example, an implantable heart stimulation device can with simple measures be constructed to constitute a device according to the invention.

It should be noted that with naturally varying heart rate is in this document meant that the heart rate is the heart rate of a heart that at the occasion in question is not paced at all by a heart stimulating device, or, if the heart is paced, then the pacing pulses are delivered in accordance with the intrinsic rate of the heart.

It should also be noted that as a measure of the heart rate, for example the duration of the heart beat can be used (since the duration of a heart beat is the inverse of the heart rate). The duration can be detected, for example as the RR-interval, i.e. the time between two R-waves. The heart rate may thus be determined for an individual heart beat.

According to an embodiment of the invention, the control circuit is configured to carry out the steps for at least three different heart rates such that the information that indicates the stroke volume as a function of the heart rate can be determined with a sufficiently high accuracy.

Since the control circuit is configured to carry out the steps for at least three different heart rates, the stored information concerning stroke volume as a function of the heart rate can be determined with a high accuracy. Preferably, the control circuit is configured to carry out the steps for more than three different heart rates, for example for at least 5 different heart rates. Thereby it can be determined with even higher accuracy how the stroke volume varies as a function of the heart rate. Consequently, very accurate information about the status of the heart can be obtained.

According to an embodiment, the control circuit is configured to carry out the steps for different heart rates, which differ from each other such that the highest heart rate is at least 10%, preferably at least 25%, higher than the lowest heart rate. Thereby, the stoke volume as a function of the heart rate can be determined for a relatively large variation of the heart rate, which means that a very good information concerning the status of the heart is obtained.

According to a further embodiment, the control circuit is configured to create a warning message if the obtained information that indicates the stroke volume as a function of the heart rate fulfils a predetermined criterion.

The predetermined criterion may for example be that the information that indicates the stroke volume as a function of the heart rate indicates that the stroke volume decreases when the heart rate increases. Another criterion may be that the information that indicates the stroke volume as a function of the heart rate indicates that the stroke volume decreases more than a predetermined amount when the heart rate increases.

With such a warning message, for example the patient in question or a physician can be alerted. The warning message may be any kind of warning message. The warning message may for example be stored in the memory. Such a warning message may for example be transferred in a wireless manner to an external device, located outside of the living being. Such a warning message may be communicated to the living being in which the device is implanted or to a physician.

According to a further embodiment, the control circuit is configured to, for a certain heart rate, derive the information correlated to the stroke volume during a plurality of heart beats, such that a more accurate information correlated to the stroke volume at the heart rate in question is obtained than if the information is derived only during one heart beat.

It should be noted that when it is said that the control circuit is configured to, for a certain heart rate, derive the information correlated to the stroke volume during a plurality of heart beats, this does not mean that the heart rate must be exactly the same for the number of heart beats. For example, the information correlated to the stroke volume for a certain heart rate may be derived for 10 different heart beats with heart rates varying between 72 and 75. From this procedure it is possible to determine for example an average measure of the stroke volume, and an average heart rate within the interval 72 to 75. Thereby a measure of the stroke volume at the heart rate in question is obtained. Hereby a more accurate information correlated to the stroke volume at the heart rate in question is obtained than if the information is derived only during one heart beat.

According to a further embodiment, the control circuit is configured such that the number of different occasions takes place within a first time period.

The time period may for example be less than 24 hours, preferable less than 1 hour, for example less than 20 minutes.

According to a further embodiment, the control circuit is configured such that the number of different occasions will also take place within at least one second time period, at a later time than the first time period, such that the memory comprises information that indicates the stroke volume as a function of the heart rate both within the first time period and within said second time period, wherein said memory contains information as to whether the indicated stroke volume as a function of the heart rate has changed between said first and second time periods.

The first and second time periods should thus not overlap with one another. The second time period may for example take place at least 1 day, or at least one week, after the first time period. By determining the stroke volume as a function of the heart rate during different time periods, it is possible to monitor how the heart condition has changed between these time periods.

According to a further embodiment, the control circuit is configured to create a warning message if the indicated stroke volume as a function of the heart rate has changed more than a predetermined amount between said first and second time periods. For example, a warning message may be created if the function determined in the second time period indicates that the diastolic dysfunction has become worse, for example indicated by the fact that the stroke volume decreases more with increasing heart rate than during the first time period.

The warning message may be any kind of warning message, for example as explained above.

According to a further embodiment, the device has a detector for detecting the physical activity of the living being, and the control circuit is configured to be able to determine the occasions when the steps are to be carried out in dependence on physical activity sensed by the detector for detecting the physical activity.

Since, the control circuit is configured to select said number of occasions in dependence on the physical activity sensed by said detector, it is possible to obtain the information that indicates the stroke volume as a function of the heart rate within a relatively short time. With the help of the sensed physical activity, it is thus possible to determine whether the physical activity of the living being changes, such that the heart rate is likely to change. It is thereby possible to obtain the information correlated to the stroke volume for different heart rates in a relatively short time. For example, each of the mentioned first and second time periods may be shorter than 20 minutes.

Alternatively, it is of course also possible for the device to directly monitor the heart rate of the living being and to select the different occasions when suitable, different heart rates are detected, such that the information that indicates the stroke volume as a function of the heart rate is obtained.

According to a further embodiment, the control circuit is configured to derive the information correlated to the stroke volume of said heart by carrying out an impedance measurement that indicates how the amount of blood in the left ventricle of the heart varies with time, which measurement thus creates a signal that varies with time, and thereby constitutes a curve that indicates how the amount of blood in the left ventricle of the heart varies with time.

Such an impedance measurement is an advantageous, and relatively simple, manner of determining the information that is correlated to the stroke volume.

According to a further embodiment, the control circuit is configured to derive the information correlated to the stroke volume either from the aforementioned curve, from a filtered such curve, from a template based on different such curves from different heart beats or from a template based on different filtered such curves from different heart beats.

The detected impedance curve may thus be filtered, for example in order to filter out artefacts and in order to make the curve smoother. A template can be created based on a measurement during a plurality of heart beats. The template is thus a representative curve based on measurements for a plurality of heart beats. The template may thus be a kind of average, or typical curve based on measurements for different heart beats.

According to a further embodiment, said information correlated to the stroke volume is derived by considering one or both of the following:
 a) an area defined by the curve, filtered curve or template,
 b) a peak-to-peak value of the curve, filtered curve or template.

In for example these manners, a good indication of the stroke volume can be obtained.

According to a further embodiment, the control circuit is configured to determine whether the contraction of the ventricle at the occasion in question belongs to a special category, and if this is the case, then the control circuit is either configured not to store the derived information in the memory, or to store the derived information separately in said memory such that the memory contains information that the derived information relates to the special category such that the stored information in the memory is distinguished from the information obtained when the contraction does not belong to the special category.

According to a further embodiment, the control circuit is configured to determine whether the contraction of the ventricle at the occasion in question belongs to any of a number of different special categories, and depending on to which special category the contraction belongs, the control circuit is either configured not to store the derived information in the memory, or to store the derived information separately in the memory, depending on the category, such the stored information in the memory for the different special categories can be distinguished from one another.

For example, the control circuit can be configured to be able to detect one or more of the following special categories (in addition to normal sinus rhythm):
 a) whether the contraction of the ventricle at the occasion in question is a premature ventricular contraction,
 b) whether the contraction of the ventricle at the occasion in question relates to atrial fibrillation,
 c) whether the contraction of the ventricle at the occasion in question is a supraventricular extra-systole,
 d) whether the contraction of the ventricle at the occasion in question is caused by left ventricular pacing,
 e) whether the contraction of the ventricle at the occasion in question is caused by right ventricular pacing,
 f) whether the contraction of the ventricle at the occasion in question is caused by biventricular pacing.

For different such special categories, the heart may behave differently, such that the mentioned information that indicates the stroke volume as a function of the heart rate may depend on the type (or category) of heart beat. For example, for heart beats that are premature ventricular contractions (PVCs), the mentioned information that indicates the stroke volume as a function of the heart rate may change more when the heart condition becomes worse than for heart beats that are not PVCs. Consequently, it is an advantage of the invention that the information that indicates the stroke volume as a function of the heart rate is stored separately for, for example, PVCs. The stored information based on PVC beats may thus be more sensitive to a change in the heart condition and will therefore be suitable to use in order to monitor a change in the heart condition.

Another aspect of the invention relates to a method of monitoring a heart of a living being with the help of an implantable heart monitoring device. The method includes the following steps:
 a) detect the heart rate,
 b) derive information correlated to the stroke volume of the heart at the detected heart rate, and
 c) store the detected heart rate and the derived information correlated to the stroke volume,
 wherein the method also includes the following steps:
 carry out steps a) to c) at a number of different occasions at different, naturally varying, heart rates, such that information that indicates the stroke volume as a function of the heart rate is obtained.

Such a method provides advantages corresponding to those described above in connection with the device according to the invention.

DESCRIPTION OF THE PREFERRED EMBODIMENTS

Figure 1:
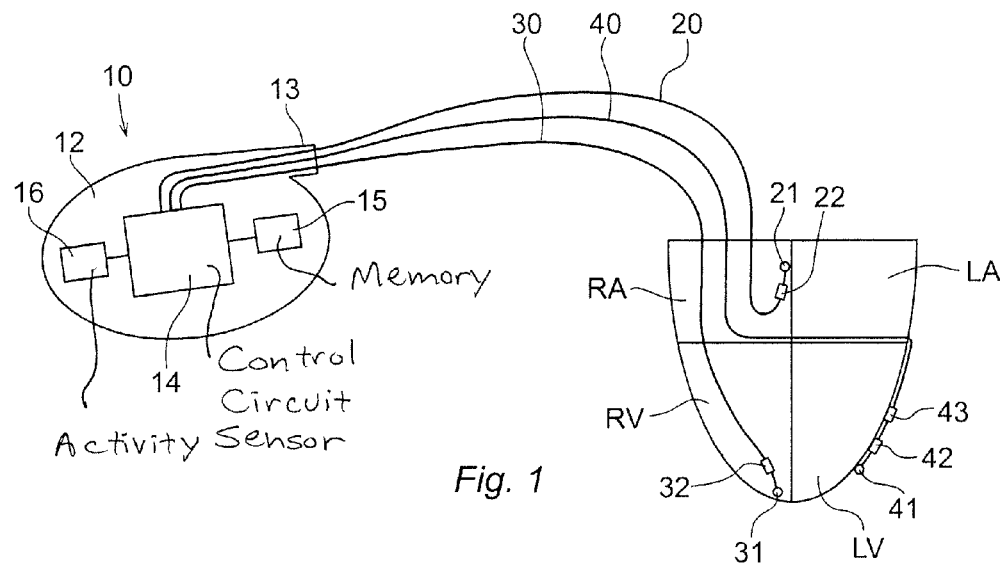
FIG. 1 shows schematically an implantable heart monitoring device with leads and electrodes positioned in or in relation to a heart.

FIG. 1 shows schematically an embodiment of an implantable heart monitoring device 10 according to the invention. The device 10 has a casing 12. The device 10 also has a control circuit 14, which controls the operation of the device 10. The device 10 also includes a memory 15 connected to the control circuit 14. Furthermore, the device 10 has an activity sensor 16 for sensing how physically active the living being that carries the device 10 is. The sensor 16 is connected to the control circuit 14.

The device 10 has a connector portion 13, via which the device 10 can be connected to different leads 20, 30, 40. According to this embodiment, there are three leads 20, 30, 40. However, the number of leads can also be more or less then three. The leads 20, 30, 40 are provided with electrode surfaces 21, 22, 31, 32, 41, 42, 43. The electrode surfaces 21, 31, 41 are so-called tip electrodes, while the other electrode surfaces 22, 32, 42, 43 are so-called ring electrodes.

The device 10 is a heart monitoring device. However, the device 10 may also have means for pacing a heart. Furthermore, the device may be designed to also function as a defibrillator. It should be noted that the device may have many more components and functions which are normal for such devices.

According to the present embodiment, the implantable heart monitoring device 10 is set up to be able to sense the electrical activity of the heart and to pace different heart chambers. In the shown embodiment, the lead 20 has been introduced into the right atrium RA such that the electrode surfaces 21, 22 are positioned in this atrium. The lead 30 has been introduced into the heart such that the electrode surfaces 31, 32 are positioned in the right ventricle RV. The electrode surfaces 21, 22 can thus be used to sense and pace the right atrium RA and the electrode surfaces 31, 32 can be used to sense and pace the right ventricle RV. LA represents the left atrium of the heart. According to this example, no electrodes are positioned to pace the left atrium LA.

The lead 40 has been introduced via the right atrium RA and the coronary sinus such that the electrode surfaces 41, 42,

43 are positioned in a vein next to the left ventricle LV. The different electrode surfaces 41, 42, 43 can thus be used to pace and sense the left ventricle LV in a manner known to a person skilled in the art. In this example, the lead 40 has three different electrode surfaces 41, 42, 43 which make it possible to choose which electrode surfaces are to be used for sensing and pacing.

It is also well-known to a person skilled in the art that different electrode surfaces can be used for injecting a current and for sensing a voltage in order to measure an impedance across at least a portion of the heart. Also the casing 12 can be used for this purpose.

Figure 2:
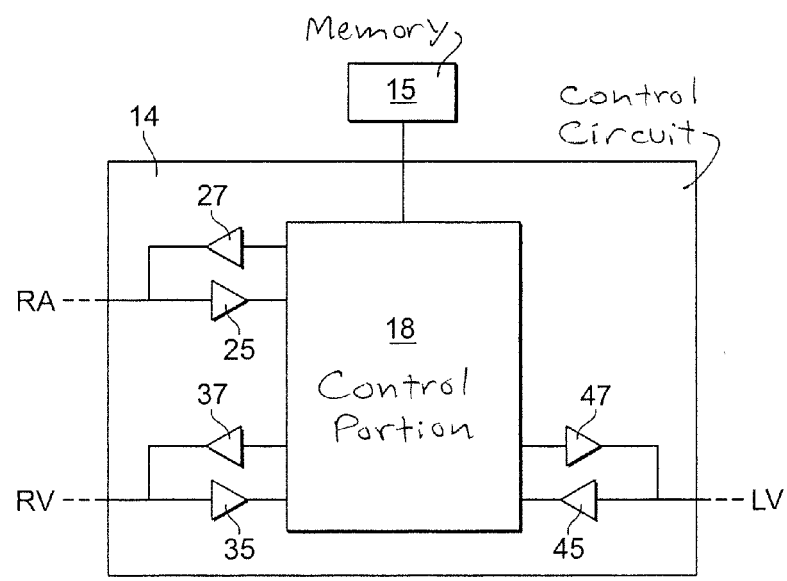
FIG. 2 shows schematically a control circuit and a memory which are comprised in the heart monitoring device.

FIG. 2 shows schematically in particular the control circuit 14 in some more detail. The control circuit 14 comprises a control portion 18 that controls the operation of the control circuit 14. The control portion 18 is connected to the above mentioned memory 15. Furthermore, as is known to a person skilled in the art, the control circuit 14 may comprise a sensing circuit 25 and a pacing circuit 27, which circuits are adapted to be connected to the lead 20 in order to pace and sense the right atrium RA. Moreover, a sensing circuit 35 and a pacing circuit 37 are adapted to be connected to the lead 30 in order to sense and pace the right ventricle RV. Furthermore, a sensing circuit 45 and a pacing circuit 47 are adapted to be connected to the lead 40 in order to sense and pace the left ventricle LV. The different sensing and pacing circuits are of course also connected to the control portion 18. The control circuit 14 may be designed such that it is possible to select which of the electrode surfaces 21, 22, 31, 32, 41, 42, 43 that are to be used. Of course, also the leads 20, 30 may be provided with more or less than two electrode surfaces.

The control circuit 14 is configured to operate in time cycles corresponding to heart cycles. This is normal for an implantable heart monitoring or pacing device.

The control circuit 14 is also configured to communicate with a number of electrode surfaces 12, 21, 22, 31, 32, 41, 42, 43 and to measure an impedance with the help of at least two such electrode surfaces. The impedance indicates the impedance across a portion of the heart that includes at least a part of the left ventricle LV. How to measure such an impedance is known to those skilled in the art, for example from some of the above-mentioned documents. For example, the control circuit 14 can be configured to inject a current between the electrode surfaces 31 and 41 and to measure a voltage between the electrode surfaces 32, 42. However, other combinations of electrode surfaces can be used for the impedance measurement. However, the control circuit 14 is preferably set up such that the variation of the measured impedance is related to the variation in the amount of blood in the left ventricle LV.

Figure 3:
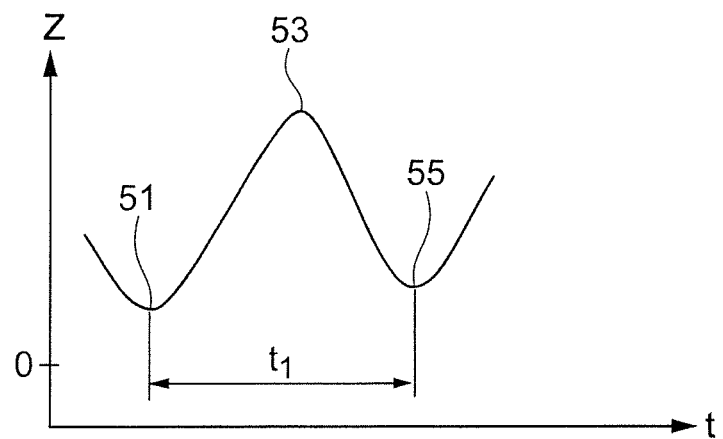
FIG. 3 show a schematic example of measured impedance as a function of time.

FIG. 3 shows schematically an example of how the measured impedance Z may vary with time t. This schematic curve in FIG. 3 is rather smooth. Such a curve can be obtained by filtering the measured impedance. The impedance is in this case measured across the left ventricle LV. The impedance has a low value at the point 51 when the left ventricle LV is filled with blood. The impedance increases thereafter until a maximum value 53 is obtained when the left ventricle LV contains a minimum amount of blood. Thereafter, the impedance decreases until a new minimum value 55 is obtained when the left ventricle LV is again filled with blood. The time $t_1$ between the minimum values 51 and 55 represents the duration of a heart beat. The heart rate is the inverse of this time $t_1$. The heart rate may for example be determined by means of the intracardial electrogram detected by the implanted device.

From the curve shown in FIG. 3 information correlated to the stroke volume SV can be obtained. As a measure of the stroke volume, for example, the peak to peak value between the minimum 51 and the maximum 53 can be used. Another alternative is to use an area defined by the curve as a measure of the SV. The area can for example be defined as the area between the curve and a predetermined base line, which for example can be the Z value indicated as 0 in FIG. 3. In this manner a value of the stroke volume SV for the heart rate in question can be determined.

In order to improve the measurement of the SV, it is possible to determine a curve like the one shown in FIG. 3 for different heart beats but with essentially the same heart rate. From such different curves, a template may be formed that represents an average of the measured curves for the different heart beats at the heart rate in question.

The control circuit 14 is configured to detect the heart rate and to derive the mentioned information correlated to the stroke volume at the detected heart rate. The control circuit 14 will store the detected heart rate and the corresponding value correlated to the SV in the memory 15.

Furthermore, the control circuit 14 is configured to carry out these steps at a plurality of different heart rates, for example for at least five different heart rates. The highest heart rate may thereby be at least 25% higher than the lowest heart rate. The different heart rates should be naturally varying heart rates as defined above. By storing the information related to the SV for the different heart rates in the memory 15, the memory 15 will comprise information that indicates the stroke volume as a function of the heart rate.

Figure 4:
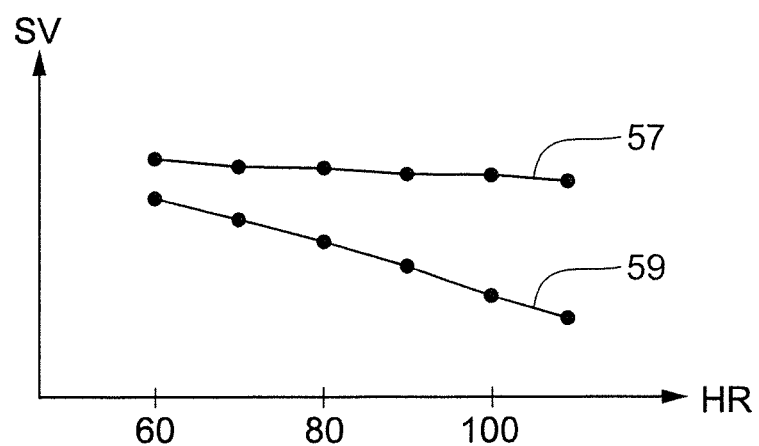
FIG. 4 shows schematically examples of how the stroke volume may vary as a function of the heart rate for different heart conditions.

Such information is schematically illustrated in FIG. 4. This Figure shows the determined stroke volume SV as a function of the heart rate HR for two different situations represented by the functions 57 and 59. Each dot represents the determined stroke volume for a certain heart rate. The function 57 may for example have been determined for a certain patient within a first time period (for example within an hour a certain day). The function 59 may have been obtained for the same patient during a second time period, for example a month later. Each function 57, 59 thus represents the status of the heart at the time that the function in question was determined. For the function 57, the stroke volume does not decrease much when the heart rate increases. However, for the function 59, the stroke volume decreases more when the heart rate increases. This is an indication of the fact that the diastolic function of the heart is worse for the function 59 than for the function 57. The heart condition of the patient in question has thus become worse.

Instead of storing all the measurement values in the memory 15, it is possible to only store information that indicates the heart condition at the time period in question. For example the slope of the function 57 and 59, respectively, can be the stored value that represents the heart condition.

The control circuit 14 may be configured to create a warning message, for example if for a certain function the stroke volume SV decreases more than a predetermined amount with increasing heart rate HR (if the negative slope of the function is higher than a predefined value).

The control circuit 14 may be configured to determine the functions (like 57 and 59) during different time periods as exemplified above. The control circuit 14 may thereby be configured to create a warning message if the indicated stroke volume as a function of the heart rate has changed more than a predetermined amount between the different time periods. The warning message may for example be created if the heart condition has become worse. For example, since the heart condition represented by the function 59 is worse than the heart condition represented by the function 57, this means that a warning message may be created in this case.

In order to determine the occasions when the control circuit 14 is to carry out the measurements in order to determine the stroke volume as a function of the heart rate, the detector 16 for detecting the physical activity of the patient in question may be used. For example, the control circuit 14 may detect that the patient is physically active such that the heart rate is likely to change. Thereby the measurement steps can be carried out for the different heart rates such that a function as described above can be determined within a relatively short time period.

Preferably, the control circuit 14 is configured to determine the kind of heart beat that is involved when the stroke volume at the heart rate in question is determined. The control circuit 14 can thereby be configured to categorize the contraction of the ventricle in different categories depending on the kind of contraction. The contraction may for example be categorized as a normal sinus rhythm, as a premature ventricular contraction, as a contraction occurring during atrial fibrillation, as a supraventricular extra-systole or as a contraction caused by pacing (left ventricular pacing, right ventricular pacing or biventricular pacing). The control circuit 14 can thereby be configured to store the derived information regarding the stroke volume at the heart rate in question separately in the memory 15 for the different categories of heart contractions. Thereby a function like the ones represented in FIG. 4 can be determined separately for the different categories of heart beats.

Figure 5:
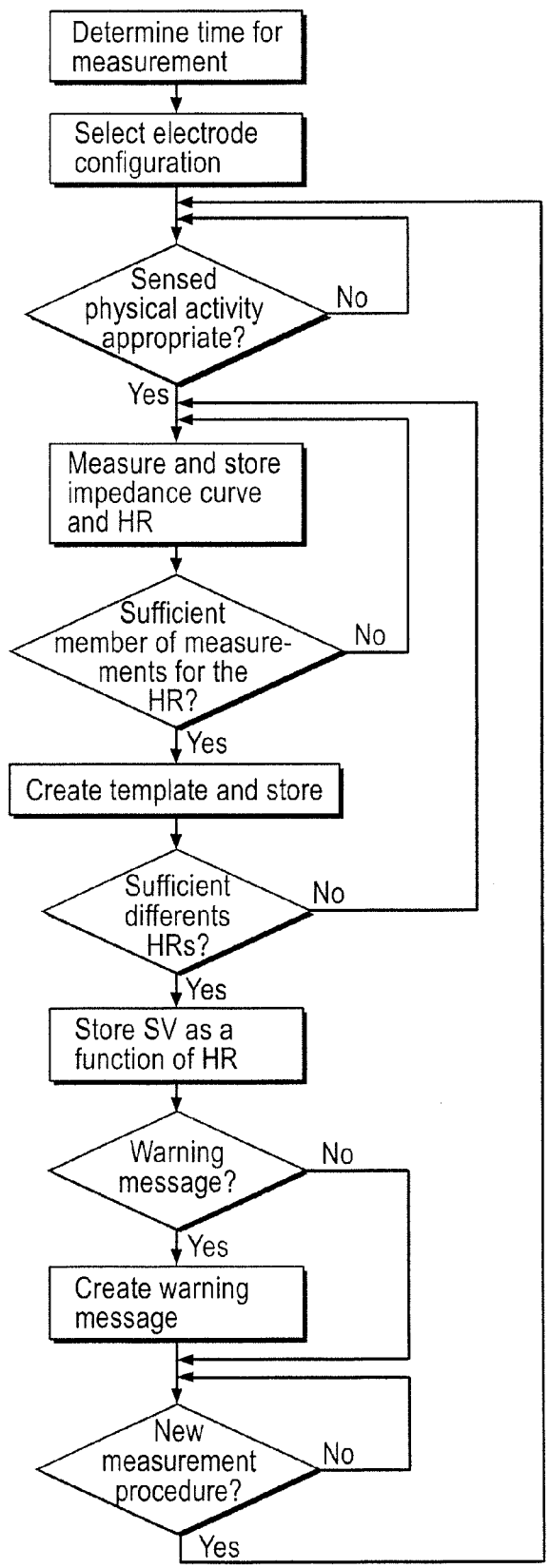
FIG. 5 is a schematic flow chart illustrating a method according to the invention.

FIG. 5 shows a schematic flow chart illustrating a method according to the invention. At the same time FIG. 5 illustrates how the device 10 according to the invention can be set up to operate.

First it is determined when to carry out the measurement with the help of the device 10. For example, it can be programmed into the device 10 that the measurements in question are to be carried out once a week.

Next, an electrode configuration for carrying out the impedance measurement is determined. This can be programmed into the device in advance, or the device 10 can automatically select an appropriate electrode configuration for the measurement. For example, as indicated above, the measurement can be carried out by injecting a current between the electrode surfaces 31 and 41 and by measuring a voltage between the electrode surfaces 32 and 42.

Next, with the help of the detector 16, the physical activity of the patient is detected in order to determine if it is appropriate to carry out a measurement. Alternatively, the exact moments for carrying out the measurements may be determined in other manners. For example, the heart rate may be detected and if the heart rate is suitable to carry out the measurement, a measurement may be carried out.

Thereafter the impedance is thus measured during a heart beat at a certain heart rate. Preferably, the impedance curve is determined for a plurality (for example at least five) of heart beats at a certain heart rate. A template may thus be created. This template constitutes a representative curve for the measured impedance during a heart beat at the heart rate in question. The determined impedance curve, or the corresponding value representing stroke volume, is stored together with the heart rate.

As mentioned above, the stored information can be stored separately for different categories, depending on the kind of heart contraction. The different heart contractions that are used to create a template for the category in question should thus be of the same kind.

The same procedure is carried out for different heart rates until sufficient information is obtained in order to determine the stroke volume as a function of the heart rate. The stroke volume as a function of the heart rate, or a corresponding value thereof, is stored. The stored information is preferably stored separately for the different categories of heart contractions.

A warning message may be created if the information concerning the stroke volume as a function of the heart rate (for a certain category) fulfils a predetermined criterion. The criterion may for example be that the stroke volume decreases more than a predetermined amount when the heart rate increases.

The procedure described above is repeated at a later occasion, for example a week later. Thereby new information is obtained that indicates the stroke volume as a function of the heart rate. A warning message may then for example be created if the heart condition has become worse.

The warning message may for example be stored in the memory 15 in order to be communicated to a device external of the patient. The warning message may for example be communicated to a physician. Of course, not only the warning message but also other stored information may be communicated to an external device.

Although modifications and changes may be suggested by those skilled in the art, it is the intention of the inventors to embody within the patent warranted heron all changes and modifications as reasonably and properly come within the scope of their contribution to the art.

We claim as our invention:

1. An implantable heart monitoring device comprising:
    a control circuit having an input that receives a signal from at least one electrode that senses a parameter related to cardiac activity;
    a memory in communication with said control circuit; and
    said control circuit being configured to (a) detect the heart rate of the subject from said signal (b) derive information correlated to the stroke volume of the heart at the detected heart rate, and (c) store the detected heart rate and the derived information correlated to the stroke volume in said memory, and said control circuit being configured to automatically execute (a), (b) and (c) at a plurality of different occasions for different, naturally varying heart rates, to enter information into said memory to produce a representation in said memory of the stroke volume as a function of the heart rate;
    wherein said control circuit is configured to operate said electrode to execute a measurement as to how an amount of blood in the left ventricle of the heart varies with time, and to derive said information correlated to the stroke volume of the heart from a result of said measurement;
    wherein said control circuit is configured to generate a curve, as said result of said measurement, indicating how said amount of blood in the left ventricle varies with time, and to derive said information correlated with the stroke volume from the curve or by an operation on said curve selected from the group consisting of filtering said curve, analyzing a template based on different curves for different heartbeats, and generating and analyzing a template based on filtering different curves for respectively different heartbeats; and
    wherein said control circuit is configured to derive said information correlated to the stroke volume from a characteristic of said curve, said filtered curve or said template, selected from the group consisting of an area and a peak-to-peak value.

2. An implantable heart monitoring device as claimed in claim 1 wherein said control circuit is configured to execute (a), (b) and (c) for at least three different heart rates.

3. An implantable heart monitoring device as claimed in claim 1 wherein said control circuit is configured to execute (a), (b) and (c) for different heart rates that differ from each other by at least 10% between a highest of said different heart rates and a lowest of said different heart rates.

4. An implantable heart monitoring device as claimed in claim 1 wherein said control circuit is configured to emit a warning signal if said information entered into said memory indicates that said stroke volume as a function of said heart rate satisfies a predetermined criterion.

5. An implantable heart monitoring device as claimed in claim 1 wherein said control circuit is configured to, for a predetermined heart rate, derive said information correlated to the stroke volume during a plurality of heartbeats.

6. An implantable heart monitoring device as claimed in claim 1 wherein said control circuit is configured to execute (a), (b) and (c) at a plurality of different occasions that occur within a predetermined time period.

7. An implantable heart monitoring device as claimed in claim 6 wherein said predetermined time period is a first predetermined time period, and wherein said control circuit is configured to also execute (a), (b) and (c) during a plurality of further different occasions that occur within a second predetermined time period, that follows said first predetermined time period, and to enter information into said memory indicating said stroke volume as a function of said heart rate both within said first predetermined time period and within said second predetermined time period, and wherein said control circuit is configured to identify whether a change in said stroke volume as a function of said heart rate has occurred between said first predetermined time period and said second predetermined time period.

8. An implantable heart monitoring device as claimed in claim 7 wherein said control circuit is configured to emit a warning signal if said change exceeds a predetermined amount.

9. An implantable heart monitoring device as claimed in claim 1 comprising a detector adapted to detect physical activity of said living subject, and wherein said control circuit is configured to determine said occasions for executing (a), (b) and (c) dependent on said physical activity.

10. An implantable heart monitoring device as claimed in claim 1 wherein said control circuit is configured to determine whether, at any of said plurality of occasions, contraction of the ventricle is in a predetermined category and, if so, to modify (c) by a modification selected from the group consisting of not storing said detected heart rate and said derived information correlated to the stroke volume in said memory, and storing said detected heart rate and the derived information correlated to the stroke volume in said memory with a designation indicating that the detected heart rate and the derived information correlated to the stroke volume were obtained when said contraction was in said predetermined category.

11. An implantable heart monitoring device as claimed in claim 1 wherein said control circuit is configured to determine whether, at any of said plurality of occasions, contraction of the ventricle is in any of a plurality of predetermined categories and, if so and depending on the category, to modify (c) by a modification selected from the group consisting of not storing said detected heart rate and said derived information correlated to the stroke volume in said memory, and storing said detected heart rate and the derived information correlated to the stroke volume in said memory with a designation indicating that the detected heart rate and the derived information correlated to the stroke volume were obtained when said contraction was in said predetermined category.

* * * * *